United States Patent Office

Plant Pat. 3,333
Patented May 15, 1973

3,333
CHRYSANTHEMUM PLANT

Walter H. Jessel, Jr., Doylestown, and William E. Duffett, Akron, Ohio, assignors to Yoder Brothers, Inc., Barberton, Ohio Filed Aug. 11, 1971, Ser. No. 170,934
Int. Cl. A01h 5/00
U.S. Cl. Plt.—80 1 Claim The present invention comprises a new and distinct cultivar of pot chrysanthemum plant which is a seedling of parents identified as #63471-2×57346-5. Both parents are unpatented and identified by the above numbers to distinguish the same from other parents in the breeding program.

The new cultivar offers the following unique characteristics to pot chrysanthemum growers:

(1) A beautiful bright lavender pink flower color that fades, but still holds a uniform color during high temperature periods.

(2) A bright, lively color under incandescent lights.

(3) Large cactus-like decorative flowers three to four inches in diameter.

(4) Plants that average 5 breaks per pinched plant.

(5) A spreading habit equal to or greater than the growth type of the well-known Mandalay family.

(6) Deeply indented foliage.

(7) A cultivar that provides an early, fast response thereby making it one of the most efficient varieties to grow from the standpoint of total crop time.

The new cultivar was selected from the progeny of the designated cross, and when asexually reproduced by cuttings at Barberton, Ohio, has been found to retain its distinctive characteristics through successive propagations.

Our new cultivar when grown in the vicinity of Barberton, Ohio, has a response period of approximately 8 weeks, and the following detailed description is based on observations made of the new cultivar in a greenhouse in Barberton, Ohio. The response time, blooming period, color, and total vigor may vary significantly with varying environmental conditions such as temperature, day length, and light intensity.

The following chart outlines the variation in response experienced and the suggested long day treatments for the various seasons, in Barberton, Ohio, with carbon dioxide injected into the greenhouse atmosphere when possible:

| Flowering period: | Response (weeks) and treatment |
|---|---|
| Spring | 8 medium. |
| Early summer | 9 medium. |
| Mid summer | 9 tall. |
| Late summer-early fall | 8 tall. |
| Late fall | 8 medium. |

Suggested flowering in the northern and western United States is from mid-March through mid-November; in coastal California, March through November; and in Florida, December through April.

The accompanying drawing shows the unique characteristics of the new cultivar, with the color being as nearly true as possible with color photographs of this type. Color references are made to the Munsell Color Book, 1963 edition.

Botanical classification: *Chrysanthemum morifolium.*

Bloom:

*Size.*—Approximately 3".

*Fully expanded.*—Approximately 4".

*Borne.*—Singly on disbudded plant.

*Stems.*—Strong.

*Form*—Decorative.

*Permanence.*—10–14 days.

*Color.*—Center of flower—dark lavender pink, 2.5RP5/10; base of petals—dark lavender pink, 2.5RP5/10 to dark pink, 2.5RP6/8; inside of petals—dark lavender pink, 2.5 RP5/10 to dark pink, 2.5RP6/8; reverse of petals—lavender, 10P8/6 to light lavender, 10P7/4; tonality from a distance—lavender; discoloration—lavender pink.

Petals:

*Texture.*—Smooth.

*Appearance and form.*—Open at base, broadens quickly, broad convexed keel, tapering to a sharp point; petal edges reflexed.

*Arrangement.*—Composite, whorled on a single receptacle.

*Persistence.*—Resist shatter.

*Fragrance.*—Typical chrysanthemum.

Reproductive organs:

*Stamen, anthers.*—None.

*Pollen.*—None.

*Arrangement.*—Clustered in center of flower, if present.

*Styles.*—Present in ray florets.

*Length.*—Short.

*Ovaries.*—At the base of petal attached to receptacle.

Plant:

*Form.*—Herbaceous.

*Growth*—Spreading.

*Height.*—Approximately 10" when given the recommended response and treatment as defined for the various seasons and outlined in the timetables of Yoder Brothers, Inc., Barberton, Ohio, assignee of the present invention.

*Spread.*—Approximately 13" when given the recommended response and treatment as defined for the various seasons and outlined in the Yoder timetables.

Foliage:

*Top side.*—Dark green, 7.5GY3/4.

*Size.*—4" long; 2" wide.

*Quantity.*—Numerous.

*Shape.*—Spatulate lobed.

*Texture.*—Smooth.

*Ribs and veins.*—Prominent.

*Edge.*—Deeply indented.

*Serration.*—Coarse.

*Underside.*—(Approximately) light green, 10GY4/4 but more gray.

*Stipules.*—Prominent.

We claim:

1. A new and distinct cultivar of chrysanthemum characterized as to uniqueness by its bright lavender pink flower color that is bright and lively even under incandescent lights, but during fading, still holds a uniform color during high temperature periods; unique large cactus-like decorative flowers three to four inches in diameter; plants that average 5 breaks per pinched plant; a spreading habit equal to or greater than the growth type of the Mandalay family; a unique deeply indented foliage, and by it early fast response, making it one of the most efficient varieties to grow from the standpoint of total crop time.

No references cited.

ROBERT E. BAGWILL, Primary Examiner